(12) United States Patent
Anbe

(10) Patent No.: US 9,161,392 B2
(45) Date of Patent: Oct. 13, 2015

(54) HEATING APPARATUS FOR X-RAY INSPECTION

(76) Inventor: Yoshinobu Anbe, Kanagawa (JP)

( * ) Notice: Subject to any disclaimer, the term of this patent is extended or adjusted under 35 U.S.C. 154(b) by 464 days.

(21) Appl. No.: 12/737,851

(22) PCT Filed: Feb. 25, 2010

(86) PCT No.: PCT/JP2010/052932
§ 371 (c)(1),
(2), (4) Date: Feb. 22, 2011

(87) PCT Pub. No.: WO2010/116809
PCT Pub. Date: Oct. 14, 2010

(65) Prior Publication Data
US 2011/0147364 A1    Jun. 23, 2011

(30) Foreign Application Priority Data

Apr. 7, 2009   (JP) ................................. 2009-092593
Nov. 9, 2009   (JP) ................................. 2009-270718

(51) Int. Cl.
| F27B 9/36 | (2006.01) |
| F27B 9/40 | (2006.01) |
| F27D 7/04 | (2006.01) |
| F27D 11/00 | (2006.01) |
| H05B 3/02 | (2006.01) |
| H05B 3/30 | (2006.01) |
| G01N 23/02 | (2006.01) |
| H05B 3/28 | (2006.01) |

(Continued)

(52) U.S. Cl.
CPC ................ *H05B 3/283* (2013.01); *H05B 3/262* (2013.01); *G01N 23/02* (2013.01); *G01N 23/20033* (2013.01); *H05B 2203/002* (2013.01); *H05B 2203/003* (2013.01); *H05B 2203/004* (2013.01); *H05B 2203/017* (2013.01); *H05B 2203/022* (2013.01); *H05B 2203/033* (2013.01)

(58) Field of Classification Search
CPC ............. H05B 3/283; H05B 2203/002; H05B 2203/003; H05B 2203/004; H05B 2203/017; H05B 2203/022; H05B 2203/033; H05B 3/02; F27D 11/00; G01N 27/4067; G01N 25/4826; G01N 23/20033; G01N 7/16; G01N 1/28; G01N 23/02
USPC ........ 219/385, 488, 546; 73/863.11; 356/369; 250/305–311
See application file for complete search history.

(56) References Cited

U.S. PATENT DOCUMENTS 3,374,349 A * 3/1968 Macres .......................... 250/310
3,474,245 A * 10/1969 Hifumi et al. ................. 250/310

(Continued)

FOREIGN PATENT DOCUMENTS

| CN | 201114811 Y | 9/2008 |
| EP | 1341216 A1 | 9/2003 |

(Continued)

*Primary Examiner* — Joseph M Pelham
(74) *Attorney, Agent, or Firm* — Keith Orum; Orum & Roth LLC

(57) ABSTRACT

In a heating apparatus for X-ray inspection which heats at least one surface of a sample (7) by convection to perform an X-ray inspection, a planar heater 1 formed of an X-ray transmitting material having an opening 1b for passing gas is provided at a window part 22 for making an X-ray observation of the sample. Thereby, a board can be subjected to convection heating uniformly without enlarging or complicating the apparatus.

10 Claims, 14 Drawing Sheets

(51) Int. Cl.
*H05B 3/26* (2006.01)
*G01N 23/20* (2006.01)

(56) References Cited

U.S. PATENT DOCUMENTS

| | | | |
|---|---|---|---|
| 3,495,328 A | | 2/1970 | Ziver |
| 3,624,390 A | * | 11/1971 | Watanabe ..................... 250/310 |
| 4,367,388 A | * | 1/1983 | Ishihara et al. ............... 219/685 |
| 4,501,144 A | * | 2/1985 | Higashi et al. ............. 73/204.26 |
| 4,827,761 A | * | 5/1989 | Vinegar et al. .................... 73/38 |
| 5,367,171 A | * | 11/1994 | Aoyama et al. ............ 250/443.1 |
| 5,396,574 A | * | 3/1995 | Base et al. ..................... 392/489 |
| 5,665,260 A | | 9/1997 | Kawada et al. ............ 219/467.1 |
| 5,689,542 A | * | 11/1997 | Lavering et al. ............. 378/142 |
| 5,698,856 A | * | 12/1997 | Frasca ..................... 250/440.11 |
| 5,735,993 A | * | 4/1998 | Yoshida .................. 156/345.27 |
| 5,756,962 A | * | 5/1998 | James et al. ............. 219/121.75 |
| 5,792,261 A | * | 8/1998 | Hama et al. ................. 118/723 I |
| 5,811,755 A | * | 9/1998 | McGee et al. ........ 219/137 WM |
| 5,922,223 A | * | 7/1999 | Okumura et al. ........ 219/121.43 |
| 6,337,479 B1 | * | 1/2002 | Kley .............................. 250/234 |
| 6,450,025 B1 | * | 9/2002 | Wado et al. ................. 73/204.26 |
| 6,914,220 B2 | * | 7/2005 | Tian et al. ..................... 219/408 |
| 7,417,206 B2 | * | 8/2008 | Nakamura ................. 219/444.1 |
| 7,889,843 B2 | * | 2/2011 | Watanabe ..................... 378/116 |
| 2004/0066895 A1 | * | 4/2004 | Hoshino ........................ 378/86 |
| 2005/0142036 A1 | * | 6/2005 | Kim et al. ...................... 422/99 |
| 2006/0210232 A1 | * | 9/2006 | Wu et al. ....................... 385/140 |
| 2007/0291902 A1 | * | 12/2007 | Tanaka et al. ................. 378/162 |
| 2008/0179518 A1 | * | 7/2008 | Creemer et al. .............. 250/311 |
| 2009/0154648 A1 | * | 6/2009 | Watanabe ..................... 378/116 |
| 2011/0096902 A1 | * | 4/2011 | Anbe .............................. 378/58 |

FOREIGN PATENT DOCUMENTS

| | | | | | |
|---|---|---|---|---|---|
| JP | 56-69889 | | 10/1954 | | |
| JP | 57-128482 | | 8/1982 | | |
| JP | 63-11756 | | 3/1988 | | |
| JP | 4-55792 | | 5/1992 | | |
| JP | 4-160788 | | 6/1992 | | |
| JP | 7-286945 | | 10/1995 | | |
| JP | 07286945 A | * | 10/1995 | ............... | G01N 1/28 |
| JP | 7-296955 | | 11/1995 | | |
| JP | 09-138073 | | 5/1997 | | |
| JP | 10-208855 | | 8/1998 | | |
| JP | 2001-007506 | | 1/2001 | | |
| JP | 2001-007506 | | 12/2001 | | |
| JP | 2002-164647 | | 6/2002 | | |
| JP | 2002164647 A | * | 6/2002 | ............... | H05K 3/34 |
| JP | 2005-166269 | | 6/2005 | | |
| JP | 2005166269 A | * | 6/2005 | ............... | H05B 3/20 |
| JP | 2005-227188 | | 8/2005 | | |
| JP | 2005-353712 | | 12/2005 | | |
| JP | 2006-165402 | | 6/2006 | | |
| JP | 2009-123796 | | 4/2009 | | |
| WO | WO 03107721 A1 | | 12/2003 | | |
| WO | WO 2008007721 A1 | * | 1/2008 | | |

* cited by examiner

Fig. 13
(a)
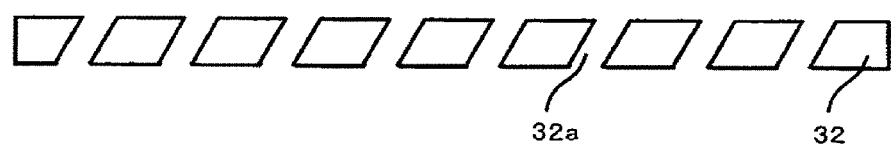
(b)
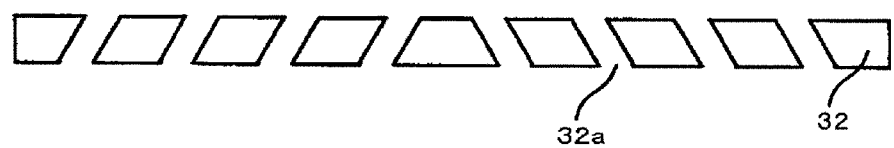
(c)

HEATING APPARATUS FOR X-RAY INSPECTION

TECHNICAL FIELD

Priority

Priority for this U.S. Nonprovisional Patent application is hereby claimed from the below mentioned application:

Foreign Applications

Japan 2009-092593 filed 7 Apr. 2009
Japan 2009-270718 filed 9 Nov. 2009

Domestic Priority

This Application is a 371 of PCT/JP2010/052932 filed 25 Feb. 2010.

The present invention relates to a heating apparatus for X-ray inspection and, in particular, to a heating apparatus for X-ray inspection which is effectively used in analyzing a cause of defective generation at a solder joint part and capable of heating an object to be examined such as a sample to a target temperature or heating it according to a predetermined profile, thereby observing and recording the change in the state in real time.

BACKGROUND ART

In recent years, an assembled circuit board has been made high in density, large in the number of layers and increasing in variety of using materials. Therefore, the necessity for an X-ray inspection capable of observing the interior or joint part of a component, in addition to conventional optical inspections has increased.

In particular, an X-ray inspection at high temperature capable of observing a change in crystalline structure or a change in the melted state by heating a sample to high temperatures can be used to observe a melted state and behavior on cooling of a solder which exists at a joint part of a component in real time. Therefore, this inspection is useful in analyzing a cause of defective generation at a solder joint part.

Where an X-ray inspection is performed on a sample under heating conditions, conventionally, there are often found cases that the sample heated outside an inspection system is set inside the inspection system and then subjected to observation. An X-ray inspection system having a heating apparatus is also proposed. However, at some of the heating elements necessary in the heating apparatus or at a part of the apparatus, a metal low in X-ray transmission is used. Since the metal absorbs, reflects, diffracts or scatters X-rays, a disadvantage is found that an X-ray receiving apparatus is unable to sufficiently receive an X-ray from an X-ray irradiation apparatus to result in a failure of conducting an accurate inspection. Thus, a heating apparatus which is capable of conducting a clear X-ray inspection under heating conditions has been required.

Further, in order to conduct an accurate inspection, it is necessary to heat a sample to high temperatures as rapidly and uniformly as in actual production. Therefore, a heating apparatus which is capable of performing rapid and uniform heating has been required. Still further, since components have been downsized, there is a growing demand for observing a very small component clearly at high magnification. In order to reduce a focal length, a heating apparatus has been required to be made thinner.

Thus, in Patent Document 1, an observation apparatus in which a heater containing a metal at some parts is separated from a sample piece to heat the sample with heated-air is proposed.

In Patent Document 2, a heating apparatus which uses ceramics formed into a plate shape as a material constituting the heating apparatus is also proposed.

In Patent Document 3, a reflow heating apparatus equipped with a heating unit which heats compressed air and feeds it is still also proposed.

However, according to the above-described conventional technologies, there has been a problem that, where a sample heated outside an inspection system is set inside the inspection system and subjected to observation, the sample decreases in temperature or unevenness in temperature distribution during the setting, thus resulting in a failure of controlling the temperature sufficiently. Further, there also has been a problem that a change in the state of the sample in association with a change in the temperature, for example, void occurrence on melting of solder or a change in a wet state, is unable to be observed accurately and in real time according to a required profile.

Further, in an X-ray inspection system equipped with heating apparatus, a metal low in X-ray transmission is used at some of the heating elements of the heating apparatus or at a part of the apparatus. And, there also has been a problem that the metal blocks the field of view for observing an X-ray image to result in a failure of making a sufficient observation.

In order to cope with these problems, the observation apparatus known by Patent Document 1 is provided with a high-temperature chamber which has a heater and a fan outside an observation path of a sample, thereby heating the sample by supplying heated-air from the high-temperature chamber.

However, in the above-described method, it has been difficult to elevate the temperature of a sample rapidly and also difficult to heat the sample in its entirety uniformly, thereby it has been difficult to control the temperature of the sample, resulting in a failure of making an observation in real time according to a required profile.

Further, the heating element is separated from the observation path, thereby an air sending passage and an air blowing mechanism of heated-air is required. Therefore, a problem is posed that a system is made larger to increase a focal length, by which it is impossible to observe a very small component clearly at high magnification. There also have been problems that an angle for observation is limited, a system is complicated and fabricated with difficulty and the system is more likely to malfunction.

In the heating apparatus known by Patent Document 2, ceramics formed into a plate shape are used as a material constituting a heating element, thereby avoiding blockage of an X-ray by the material constituting the heating apparatus. However, a problem is posed that a ceramics heater is slow in elevating temperatures, difficult in controlling temperatures, easily broken and low in durability. Further, since the heating apparatus is not provided with a mechanism for generating air flow within it, there is found a problem that unevenness in temperature distribution inside the apparatus causes.

At present, reflow soldering heating methods used for boards produced worldwide are mostly done by convection heating. This is because, in most cases, components are loaded above and below a glass epoxy board (the back surface is not flat) and therefore thermal conduction heating is not usable.

However, there is a significant difference in soldering behavior between thermal conduction heating and convection heating which is actually conducted on the market. This is because there is a difference in temperature elevation speed between various parts such as a board, a solder paste and a component and also there is a difference in the amount of the solder paste to be dried and oxidized.

For this reason, an inspection which heats an assembled circuit board by thermal conduction heating that may cause a phenomenon which does not take place in reality is meaningless in examining a mechanism of various types of soldering defects caused by convection heating. The above fact is known by technical experts of soldering as common knowledge.

Where a board is subjected to a motion image inspection with an X-ray, convection heating is needed for examining the soldering behavior which takes place in reality. However, conventional reflow heating furnaces for X-ray inspection which have been so far filed are mostly conducted by thermal conduction heating.

In addition, convection heating is described in some of the patent applications like that found in Patent Document 3. Since heated-air is supplied outside a field of view of an X-ray, the temperature distribution on a board is different from the actual temperature distribution and temperatures differ widely at various parts. Further, in the reflow heating apparatus known by Patent Document 3, heated compressed air is ejected to cause convection, thereby heating a sample. Therefore, a problem is posed that an air compressing mechanism is needed to result in a larger and complicated apparatus.

PRIOR ART DOCUMENTS

Patent Documents

[Patent Document 1] Japanese Published Unexamined Patent Application No. 2005-227188
[Patent Document 2] Japanese Published Unexamined Patent Application No. Hei-9-138073
[Patent Document 3] Japanese Published Unexamined Patent Application No. 2009-123796

SUMMARY OF THE INVENTION

The present invention has been made in view of the problems found in the above-described conventional technologies, and a first object of the present invention is to provide a heating apparatus for X-ray inspection capable of subjecting a board to uniform convection heating without enlarging or complicating the apparatus.

A second object of the present invention is to provide a heating apparatus for X-ray inspection equipped with a, heater which is low in price, high in heat resistant temperature and long in service life.

In order to solve the above-described problems, one embodiment of the invention is a heating apparatus for X-ray inspection which heats at least one surface of a sample by convection to perform an X-ray inspection characterized in that a planar heater formed of an X-ray transmitting material having an opening for passing gas is provided at a window part for making an X-ray observation of the sample.

Another embodiment of the invention is the heating apparatus for X-ray inspection described herein in which the planar heater has a shape of a spiral type, a zigzag type or a combination of the spiral type with the zigzag type.

Another embodiment of the invention is the heating apparatus for X-ray inspection described herein in which the planar heater is made of a thin metal plate which can transmit X-rays.

Another embodiment of the invention is the heating apparatus for X-ray inspection described herein in which the metal plate is reinforced with an insulating plate where a heated-air blowing hole for smooth convection is formed.

Another embodiment of the invention is the heating apparatus for X-ray inspection described herein in which the heated-air blowing hole formed, at the insulating plate on the side of a sample is formed obliquely so as to generate a swirling flow.

Another embodiment of the invention is the heating apparatus for X-ray inspection described herein in which the planar heaters are disposed so as to oppose both surfaces of a sample, thereby making it possible to effect convection heating from both surfaces of the sample.

Another embodiment of the invention is the heating apparatus for X-ray inspection described herein in which a shielded heat isolation part formed of an X-ray transmitting material having a gas supplying port is disposed on the planar heater so as to be overlapped.

Another embodiment of the invention is the heating apparatus for X-ray inspection described herein in which a heated-air blowing plate formed of an X-ray transmitting material having a heated-air blowing hole for smooth convection is disposed on the planar heater so as to be overlapped.

Another embodiment of the invention is the heating apparatus for X-ray inspection described herein in which the heated-air blowing hole is provided obliquely.

Another embodiment of the invention is the heating apparatus for X-ray inspection described herein in which the heating apparatus is constituted on rigid supporting bodies which oppose each other, the shielded heat isolation part and the planar heater are arranged on one of the window part and, of the shielded heat isolation part and the planar heater, at least the shielded heat isolation part is arranged on the other of the window part.

Another embodiment of the invention is the heating apparatus for X-ray inspection described in herein in which the heating apparatus is provided with a gas supplying pipe exclusively for cooling on the supporting bodies.

Another embodiment of the invention is the heating apparatus for X-ray inspection described in herein or herein in which the heating apparatus is provided with an exhaust opening on the supporting bodies.

Another embodiment of the invention is the heating apparatus for X-ray inspection described herein in which the heating apparatus is provided with a limit switch between rigid supporting bodies which oppose each other.

Another embodiment of the invention is the heating apparatus for X-ray inspection described herein in which a pressure sensor is disposed on a gas supplying pipe connected to a gas supplying port of the shielded heat isolation part.

Another embodiment of the invention is the heating apparatus for X-ray inspection described herein in which at least the shielded heat isolation part and the planar heater are made available as modules.

Another embodiment of the invention is the heating apparatus for X-ray inspection described herein in which the heating apparatus is a reflow furnace.

Another embodiment of the invention is a heating apparatus for X-ray inspection which is provided with a planar heater made of a thin metal plate that can transmit X-rays.

According to the heating apparatus for X-ray inspection described herein, heating is done by using gas which has passed into an opening formed on the planar heater, thus making it possible to promote convection and also finely control temperatures. Further, an atmosphere inside the heating apparatus can be controlled, by which it is possible to prevent or control combustion and oxidation and also make an observation under a specific gaseous atmosphere.

According to the heating apparatus for X-ray inspection described herein, the shape of the planar heater is formed into a zigzag type, a spiral type or a combination of the zigzag type with the spiral type, by which it is possible to control a value of electric current flowing through the heating element and voltage freely and easily. Thereby, it is possible to establish the performance, specification and standard of the heating apparatus freely and easily.

According to the heating apparatus for X-ray inspection described herein, the planar heater can be produced at a very low cost and is also made high in heat resistant temperature and long in service life.

According to the heating apparatus for X-ray inspection described herein, the planar heater can be constituted with an extremely thin metal plate.

According to the heating apparatus for X-ray inspection described herein, the heated-air blowing hole is provided obliquely, thus making it possible to generate a swirling flow inside a sample chamber and provide heating rapidly and uniformly.

According to the heating apparatus for X-ray inspection described herein, it is possible to provide convection heating from both surfaces of a sample.

According to the heating apparatus for X-ray inspection described herein, the shielded heat isolation part and the planar heater arranged so as to be overlapped can be constituted with a material favorable in X-ray transmission properties at the window part for making an X-ray inspection of a sample. Thereby, it is possible to provide a heating apparatus capable of making a clear observation under heating conditions at a free angle by using an X-ray inspection system easily.

According to the heating apparatus for X-ray inspection described herein, the planar heater and the heated-air blowing plate having the heated-air blowing hole for smooth convection are arranged so as to be overlapped. Thereby, the heating apparatus can be downsized and also a heating part can be easily made closer to a sample. Further, heated-air which has been heated by the planar heater is directly ejected through the heated-air blowing hole formed on the heated-air blowing plate. Thereby, it is possible to feed heated-air which is sufficient in temperature and wind velocity without using a blower or a pressure mechanism and without lowering temperatures on a flow path. Therefore, convection heating due to the heated-air is used to elevate the temperature of the sample rapidly and the sample in its entirety can be heated uniformly. As a result, it is possible to easily control the temperature of the sample and also make an observation in real time according to a required profile.

Use of the above-described heating system makes it possible to downsize an apparatus and bring a sample closer to an X-ray inspection system. Therefore, it is possible to observe a very small component clearly at high magnification.

Further, supply of gas makes it possible to control an atmosphere inside the heating apparatus. Therefore, it is possible to prevent or control combustion and oxidation and make an observation in a specific gaseous atmosphere.

According to the heating apparatus for X-ray inspection described herein, the heated-air blowing hole is provided obliquely, thereby making it possible to generate a swirling flow inside the sample chamber and effect rapid and uniform heating.

According to the heating apparatus for X-ray inspection described herein, the apparatus is constituted on rigid supporting bodies which oppose each other, the shielded heat isolation part and the planar heater are arranged on one surface of the window part and, of the shielded heat isolation part and the planar heater, at least the shielded heat isolation part is arranged on the other surface of the window part. Thereby, a sample can be heated by selecting various heating methods, for example, convection heating from both surfaces of the sample, convection heating from one surface and thermal conduction heating from the other surface, and convection heating from one surface and no heating from the other surface. Thus, it is possible to provide heating according to a state of the sample.

According to the heating apparatus for X-ray inspection described herein, the gas supplying pipe exclusively for cooling is provided on the supporting bodies. Thereby, it is possible to provide rapid cooling or control a cooling state. It is also possible to observe not only the influence of heating but also the influence of cooling.

According to the heating apparatus for X-ray inspection described herein, the exhaust opening is provided on the supporting bodies, thus making it possible to control temperatures inside the sample chamber and also a gaseous atmosphere easily.

According to the heating apparatus for X-ray inspection described herein, the limit switch is provided between the rigid supporting bodies, thus making it possible to prevent heating in an open state and provide a heating apparatus high in safety.

According to the heating apparatus for X-ray inspection described herein, the pressure sensor is disposed on the gas supplying pipe connected to the gas supplying port at the shielded heat isolation part. Thereby, it is possible to prevent heating without gas supply and provide a heating apparatus free of risk of overheating and high in safety.

According to the heating apparatus for X-ray inspection described herein, at least the shielded heat isolation part and the planar heater are made available as modules, thus making it possible to provide a heating apparatus excellent in maintenance properties and cost performance.

According to the heating apparatus for X-ray inspection described herein, the heating apparatus for X-ray inspection is a reflow furnace, by which it is possible to provide a reflow furnace capable of making an X-ray inspection of a board and also easy in controlling temperatures.

According to the heating apparatus for X-ray inspection described herein, the planar heater made of a thin metal plate that can transmit X-rays is provided, thus making it possible to provide a heating apparatus for X-ray inspection having a heater low in cost, high in heat resistant temperature and long in service life.

On the basis of the above description, working effects of the heating apparatus according to the invention as claimed in the application concerned are listed hereinafter.

A first effect is that an X-ray inspection system under heating conditions can be used to observe a sample clearly.

A second effect is that a sample can be heated rapidly.

A third effect is that a sample can be heated uniformly.

A fourth effect is that a sample can be heated at high temperatures.

A fifth effect is that a method for heating a sample can be selected.

A sixth effect is that a sample can be controlled for cooling.

A seventh effect is that a sample can be observed in real time.

An eighth effect is that a sample can be observed at an angle that can be established freely.

A ninth effect is that the apparatus can be made thin.

A tenth effect is that the apparatus can be made simple.

An eleventh effect is that the apparatus is high in durability.

A twelfth effect is that the apparatus can be operated safely.

A thirteenth effect is that the apparatus is high in maintenance properties.

A fourteenth effect is that the apparatus is excellent in cost performance.

Further, as a matter of common knowledge, it was thought impossible in view of X-ray transmission to use a metal plate large in atomic weight as a heater. X-ray transmission properties of a metal can be simply expressed in a manner that the transmission properties are lower as the value obtained by multiplying an atomic number with the thickness is larger. As a realistic problem, a 30 µm-thick stainless steel plate of SUS 430 was processed into a spiral type and used as a heater experimentally. This heater was excellent and free of any problems with respect to X-ray transmission properties, sufficient in heating value and found to be long in service life. The plate is made thinner to enhance the X-ray transmission properties and increase the electric resistance and therefore can be used as a heater. Further, this heater is extremely low in cost and can be processed by etching or others and also high in heat resistant temperature and long in service life.

BRIEF DESCRIPTION OF THE DRAWINGS

FIG. 13 is also a cross sectional view which shows an arrangement of heated-air blowing holes in Embodiment 3.

MODE FOR CARRYING OUT THE INVENTION

Hereinafter, a detailed explanation will be made for embodiments of the present invention by referring to drawings.

Figure 1:
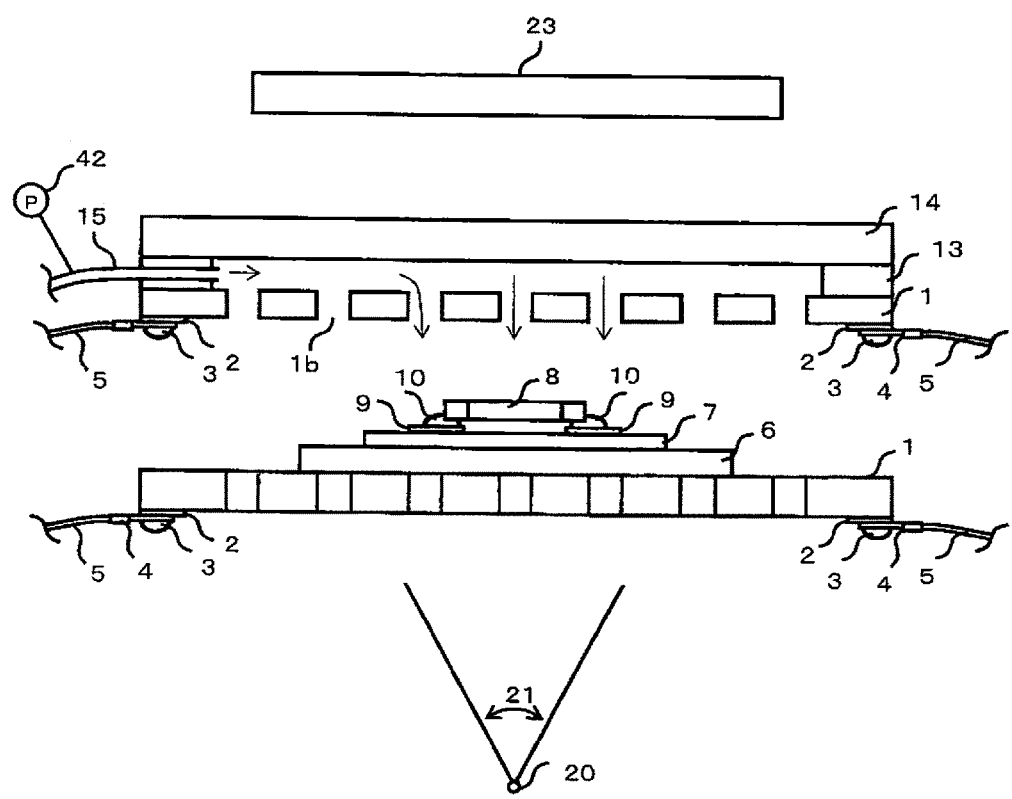
FIG. 1 is a cross sectional view which shows an entire constitution of Embodiment 1 of a heating apparatus for X-ray inspection according to the present invention.

FIG. 1 is a cross sectional view which shows an entire constitution of the heating apparatus for X-ray inspection according to the present invention. In this figure, the reference number 1 depicts a planar heater; 2, copper plate electrode; 3, screw; 4, crimp-type terminal; 5, covered conductor line; 6, insulating plate high in heat resistance and heat conductivity; 7, print circuit board; 8, electronic component soldered such as a semiconductor chip to be soldered, for example; 9, copper land; 10, solder paste; 13, sealant; 14, shielded heat isolation part; 15, gas supplying pipe; 20, X-ray generating part of X-ray irradiation apparatus; 21, X-ray irradiation range; and 23, X-ray receiving apparatus.

Figure 2:
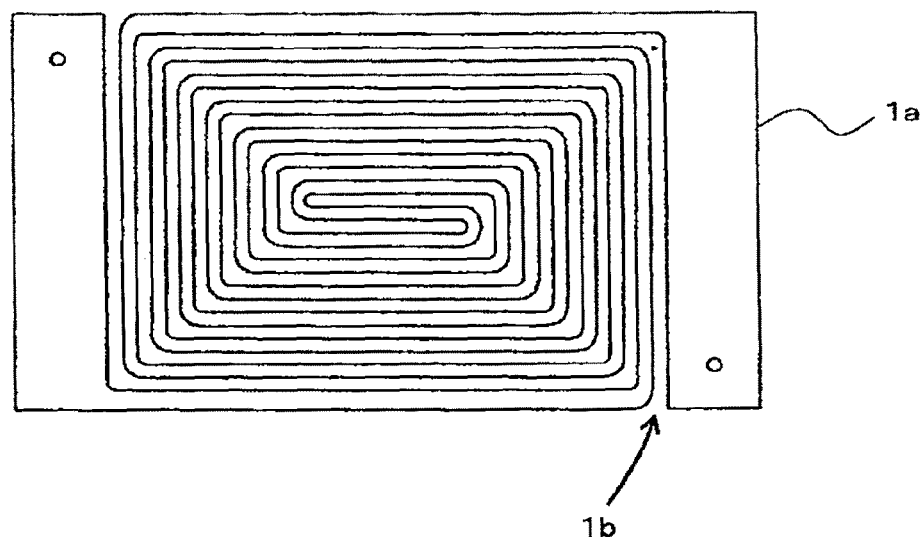
FIG. 2 is a plan view which shows the shape of a planar heater used in Embodiment 1.

The planar heater 1 is constituted with, for example, a 30 µm-thick thin stainless steel plate 1a (for example, SUS430). As shown in FIG. 2, the planar heater is given an electric resistance value suitable for a heater and provided with a slit 1b for allowing gas to pass.

Since the metal plate is extremely low in electric resistance, there is a case where a large current may flow even at a low voltage. However, adoption of a thin-plate formed in a spiral shape makes it possible to easily control electric resistance and a value of electric current. A power supply and a cable for general purpose can be used to yield a high heating value.

Figure 3:
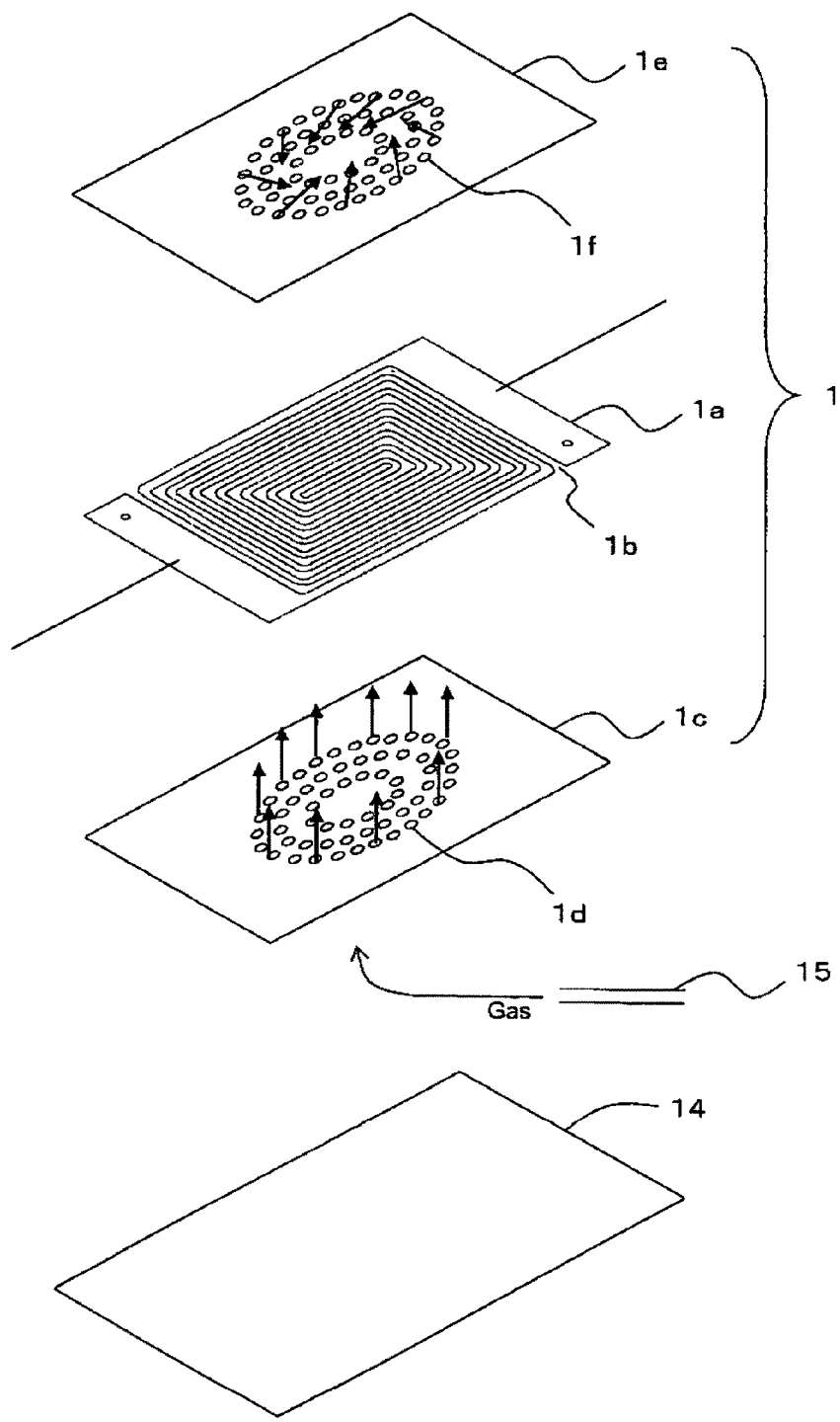
FIG. 3 is also an exploded perspective view of the planar heater.
Figure 4:
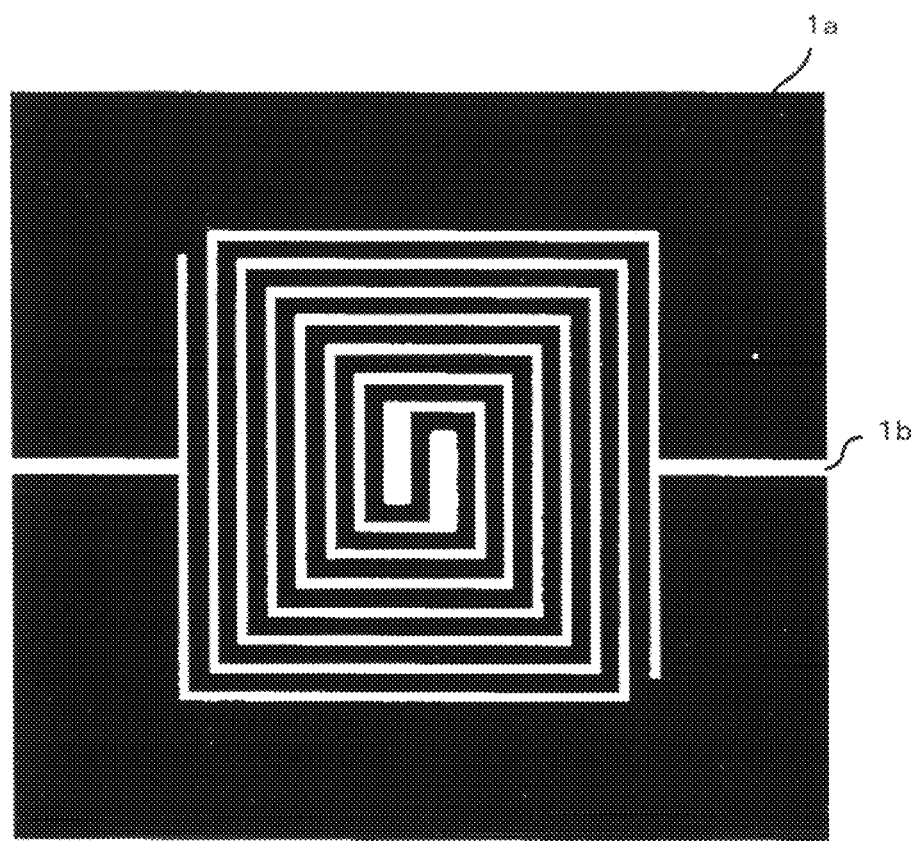
FIG. 4 is a plan view which shows the shape of another example of the planar heater.
Figure 5:
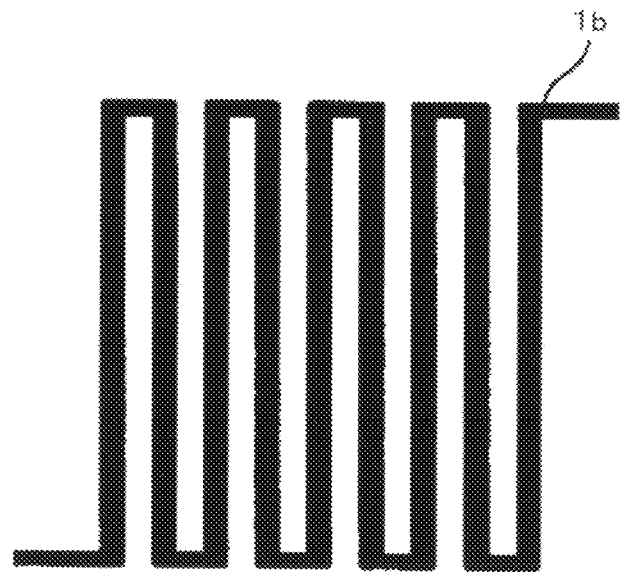
FIG. 5 is also a plan view which shows the shape of still another example.
Figure 6:
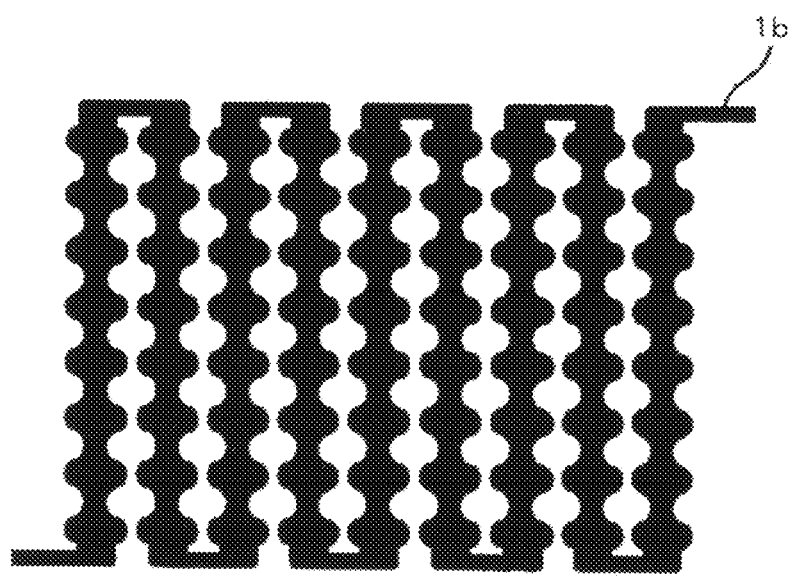
FIG. 6 is also a plan view which shows the shape of a further example.
Figure 7:
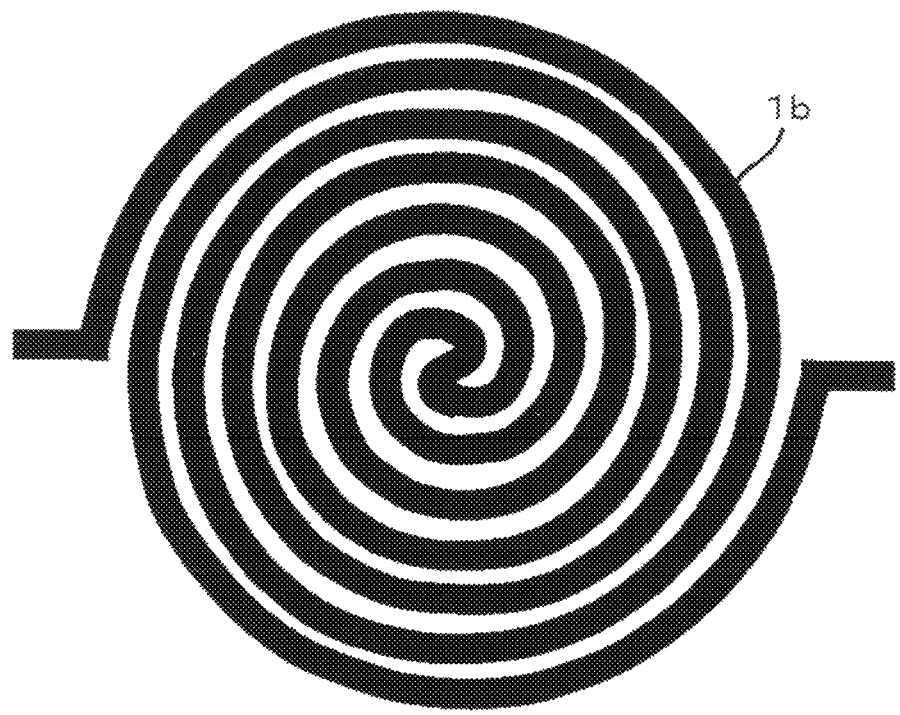
FIG. 7 is also a plan view which shows the shape of a still further example.

In addition, the heater 1a made of a metal plate is thin in thickness and therefore unable to keep the plate shape. Thus, as shown in FIG. 3 (for easy understanding, the top and the bottom are illustrated reversely unlike the case of FIG. 1), a sandwich structure is provided that, for example, 1 mm-thick insulating plates (for example, those made of boron nitride BN, ceramics and mica) 1c, 1e are used to hold the heater 1a therebetween from both surfaces. In this instance, at a site which is overlapped on the slit 1b of the heater 1a at the insulating plate 1c on the side of a gaseous space (below in FIG. 3), many gas holes 1d perpendicular to the surface of the insulating plate 1c are formed. At a site which is overlapped on the slit 1b of the heater 1a at the insulating plate 1e on the side of a sample (above in FIG. 3), many gas holes 1f oblique to the surface of the insulating plate 1e so as to generate a swirling flow are formed, such as the heated-air blowing holes 32a illustrated in FIG. 13 to be described later.

Figure 8:
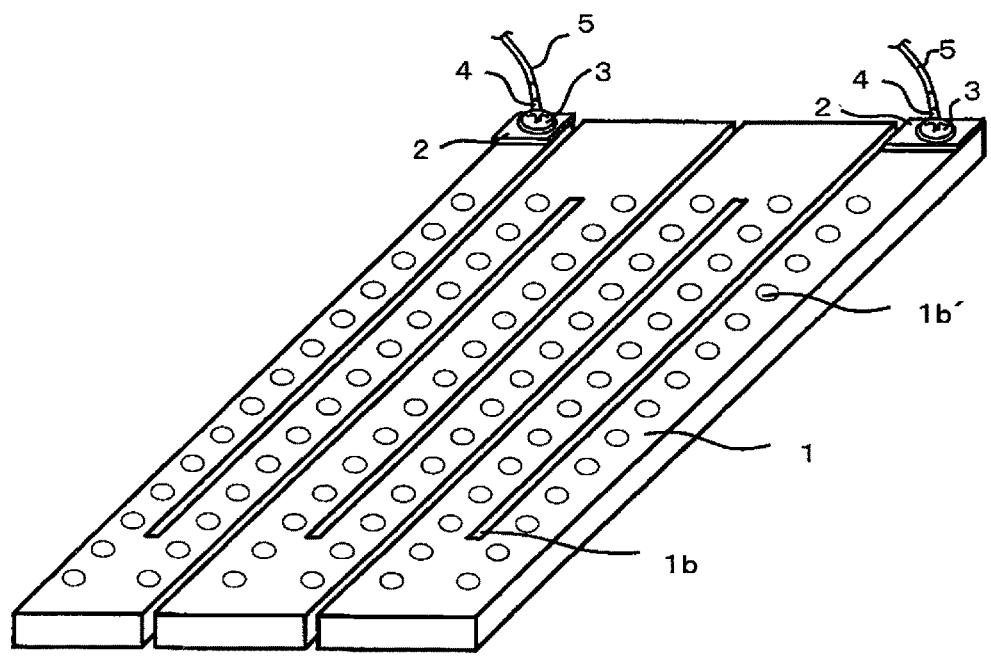
FIG. 8 is also a perspective view which shows the shape of another sample.

In addition, there is no particular restriction on the size and shape of the planar heater 1 or the structure, size and shape of the spiral type. Patterns of the spiral type and the zigzag type can be provided in various ways as shown in plan views of FIG. 4 to FIG. 7. There is no particular restriction on the patterns in addition to those shown in these figures. Where the slit 1b is narrow in width to result in insufficient gas supply, gas holes 1b' may be provided as shown in FIG. 8.

The metal plate heater 1a can be formed as a metal-resistant thin film on an insulating plate such as ceramics by vapor deposition of PVD, CVD or others, in addition to etching. It is desirable that a target to which the metal plate heater 1a is deposited is an insulating plate 1e on the side of a sample where oblique gas holes 1f are formed. In this instance, it is also possible to omit an insulating plate 1c on the side of the gaseous space.

A material of the metal plate is not restricted to an alloy of Fe—Cr such SUS 430 or other stainless steel. Other metals which can be formed into a thin film and which are heat resistant, free of deterioration due to oxidation and give resistivity usable as a heater may include alloys of Ni—Cr, Ni—Cr—Fe, Fe—Cr—Al, Cu—Mn, Cu—Ni and other metals.

In the above-constituted Embodiment 1 of the present invention, in order to activate the heating apparatus, at first, voltage is applied to a covered conductor line 5. Although it is acceptable that the applied voltage may be direct current or alternative current, the current will flow via the crimp-type terminal 4 into the copper plate electrode 2.

Further, since the planar heater 1 is firmly attached to the copper plate electrode 2 with the screw 3, the current will flow uniformly inside the planar heater 1. In this instance, the metal plate is low in electric resistance and easily electrified, by which the current flows easily to produce a heating value according to electric power.

Since heating is generated uniformly and also the metal plate in itself is high in heat conductivity, the planar heater 1 undergoes rapid and uniform temperature elevation.

A print circuit board 7, which is a sample, is installed on the planar heater 1 via an insulator 6 high in heat resistance and heat conductivity. The insulator 6 favorably includes a plate and a sheet made of alumina ceramics, polyimide resin, silicone resin, fluorocarbon resin and mica, with no particular restriction thereon. A material can be selected freely depending on a required temperature. Further, the planar heater 1 may be covered with the insulator 6.

The sample can be installed directly on the planar heater 1 only via the insulator 6 high in heat resistance and heat conductivity. Therefore, the sample can also be rapidly and uniformly heated in association with a rapid and uniform temperature elevation of the planar heater 1.

Further, the heating value can be easily controlled by controlling the voltage while being monitored with a thermoelectric couple. It is, thereby, possible to control temperatures of the sample according to a required profile.

In association with temperature elevation of the planar heater 1, the print circuit board 7, which is a sample installed on the insulator 6, undergoes rapid and uniform temperature elevation within the plane. A stainless steel plate of the present embodiment is high in heat resistant temperature and able to sufficiently fuse a solder paste 10. In association with temperature elevation, the solder paste 10 is melted to wet an electronic component 8 and a copper land 9 and join them.

Further, an observation can be made in real time in a predetermined temperature profile, which is helpful in clarifying a void developing mechanism.

Still further, since no heat transmitting mechanism is needed outside a field of view for inspection, there is no restriction on an observation angle. Therefore, an apparatus can be made thin and simplified and also produced easily. The metal plate in itself is also superior in strength, thus making it possible to easily obtain a highly durable heating apparatus.

In addition, in FIG. 1 and FIG. 2, the planar heater 1 is formed in a flat plate shape. This plate may be made round or bent, thereby making it possible to provide a cylindrical or rectangular tubular heating apparatus as described in Patent Document 2, for example.

The present embodiment is characterized in that the metal plate is directly electrified to generate heating. However, in addition to the metal plate, a planar heater which is constituted with a carbon-fiber reinforced carbon composite material plate formed of an advanced composite material made of a carbon fiber and a carbon matrix, for example, may be used. In this instance, those which meet the following three characteristics are all included in carbon-fiber reinforced carbon composite materials. In other words, a first characteristic is that there are no serious disadvantages such as oxidation and deterioration even on heating at 250° C. in the atmosphere, a second characteristic is that electric conductivity is found, and a third characteristic is that carbon fiber is contained at least partially in the material.

In addition, here, a carbon-fiber reinforced carbon composite material is to have a heat resistant temperature of 250° C. or higher. However, the carbon-fiber reinforced carbon composite material is high in heat resistance and can be heated up to a high temperature of 1000° C. or higher, if necessary. By temperature control or gas atmosphere control or forming an oxidation preventing film, an observation can be made easily under high temperature conditions. In addition to the above-described electronic component, various materials and components can be observed for the heating behavior.

Further, a carbon-fiber reinforced carbon composite material plate can be used as a sealing wall material of the present heating apparatus. Thereby, it is possible to easily obtain a heating apparatus which is light in weight, high in heat resistance, small in size, simple in constitution and high in durability.

In the present embodiment, gas which has been supplied through the gas supplying pipe 15 is allowed to pass into the slit 1b provided on the planar heater 1 and heated, by which atmosphere heating due to convection is added to heating due to contact and irradiation, thus making it possible to finely control temperatures elaborately. Not only can the speed of temperature elevation be controlled by the flow rate of the gas but also cycle operation can be conducted between temperature elevation and cooling. Further, there are advantages that oxidation and combustion can be prevented or controlled by injecting an inert gas and others, an observation can be made under a specific gas atmosphere, and a poisonous gas generated from a sample can be discharged outside to prevent adverse effects on the sample and an apparatus. Still further, after completion of observation, ambient air or cold air can be sent to cool the sample and the apparatus rapidly.

Figure 9:
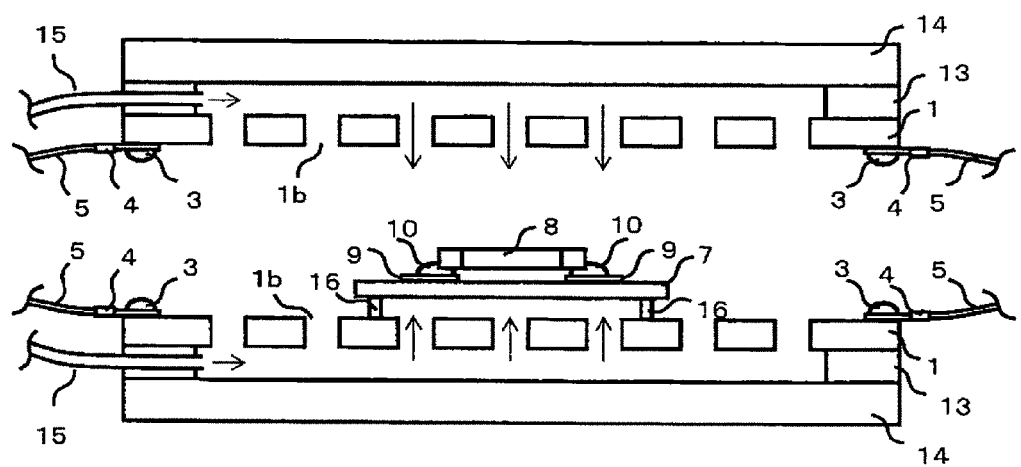
FIG. 9 is a cross sectional view which shows an entire constitution of Embodiment 2 of the heating apparatus for X-ray inspection according to the present invention.

FIG. 9 shows Embodiment 2 of the heating apparatus in which the planar heaters 1 shown in FIG. 2 and FIG. 3 are installed above and below. In the figure, the reference number 16 depicts an insulation spacer inserted between the lower planar heater 1 and the print circuit board 7.

According to the present embodiment, it is possible to conduct smooth heating by convection from above and below.

Next, a detailed explanation will be made for Embodiment 3 of the present invention which is a further improvement of Embodiment 2.

Figure 10:
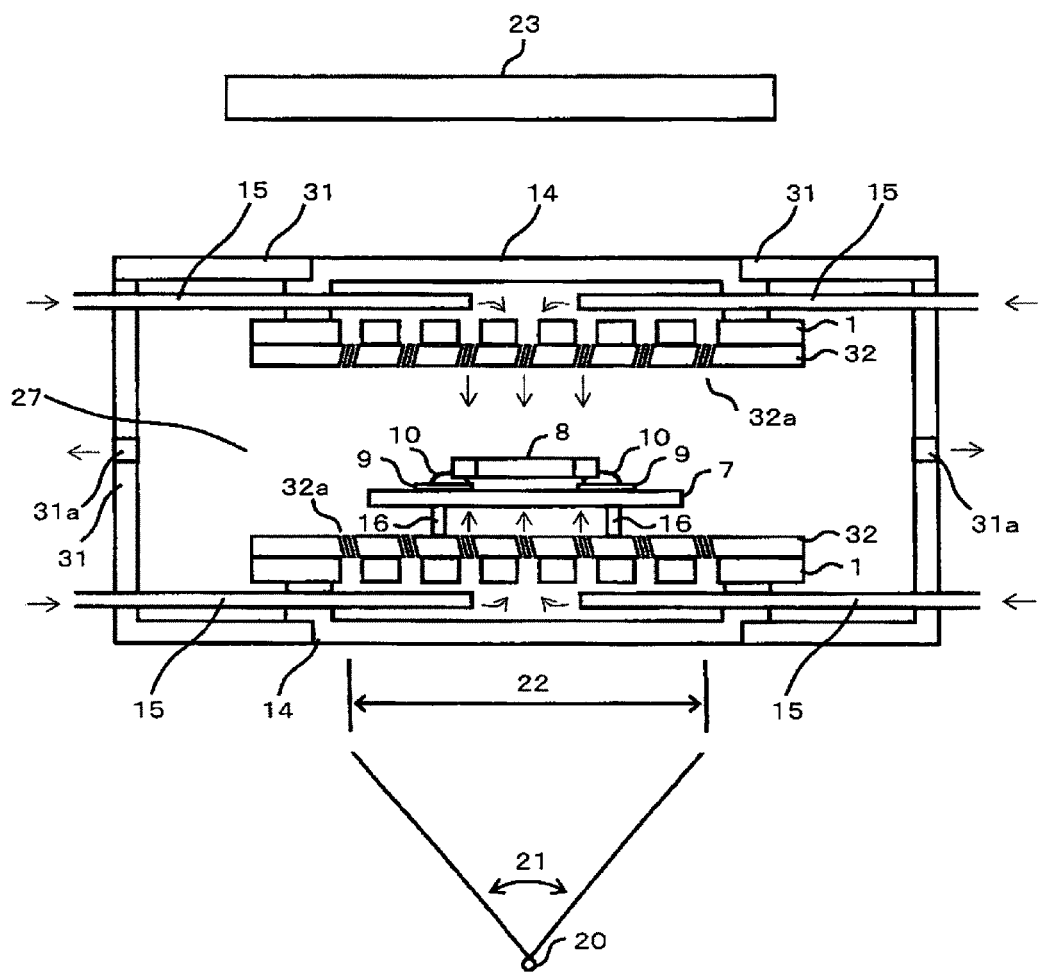
FIG. 10 is a cross sectional view which shows an entire constitution of Embodiment 3 of the heating apparatus for X-ray inspection according to the present invention.
Figure 11:
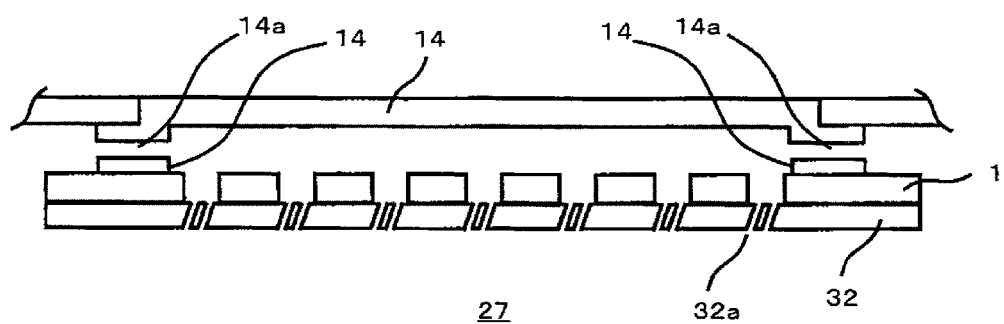
FIG. 11 is a cross sectional view which shows important constitution of Embodiment 3.

FIG. 10 is a cross sectional view for explaining Embodiment 3. In this figure, the reference number 22 depicts a window part; 32, heated-air blowing plate; 32a, heated-air blowing hole; 27, sample chamber; and 31, supporting body. Further, the gas supplying pipe 15 can be used by being fitted into heated-air blowing holes 14a on the shielded heat isolation part 14 at the heating part shown in the cross sectional view of FIG. 11. In this figure, the reference number 31a is an exhaust opening formed, for example, on a side surface of the supporting body 31. Since as for the other points, the present embodiment is similar to Embodiment 2, the same reference numbers are used to omit an explanation.

In the above-constituted Embodiment 3, in order to heat a sample, voltage is applied to the planar heater 1, with gas being supplied from the gas supplying pipe 15. The voltage may be applied from a part outside the window part 22 at the end of the planar heater 1. Further, the voltage can be applied either by direct current or alternative current. In addition, on observation, a thermoelectric couple can be installed at a part which gives no trouble in making an X-ray observation, thereby monitoring temperatures.

Further, in the figure, the heating apparatus is installed horizontally but can be installed vertically or obliquely when necessary. Various combination of methods for installing the heating apparatus with methods for setting a sample, makes it possible to observe the sample at any angle.

With an increase in temperature of the planar heater 1, gas supplied from the gas supplying pipe 15 is elevated in temperature, by which heated-air is blown from the heated-air blowing holes 32a to generate a heated swirling flow inside the sample chamber 27 and elevate the temperature inside the sample chamber 27. Then, the print circuit board 7, which is a sample, is also elevated in temperature rapidly and uniformly inside the plane, and the solder paste 10 is melted to wet the electronic component 8 and the copper land 9 and join them.

In the heating apparatus of the present invention, since only a material excellent in X-ray transmission properties is used at the window part 22 which is an X-ray observation range of a sample, it is possible to observe the wetting behavior of solder clearly under various temperature conditions.

Further, a real-time observation can be made in a predetermined temperature profile, which is helpful in clarifying a void developing mechanism.

Still further, since no heat transmitting mechanism from outside is needed, it is possible to downsize and make thinner an apparatus. Therefore, it is possible to bring a sample closer to an X-ray inspection system and observe a very small component clearly at high magnification.

Figure 12:
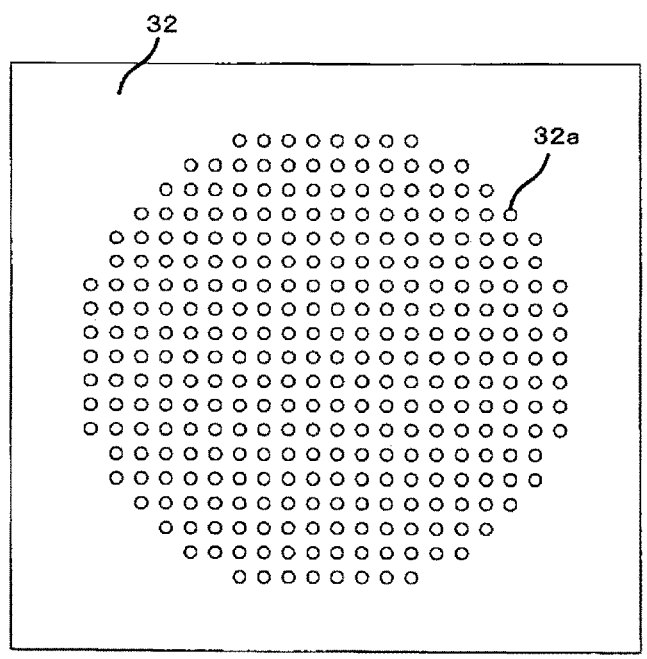
FIG. 12 is a plan view which shows a constitution of a heated-air blowing plate used in Embodiment 3.

The heated-air blowing holes 32a are provided minutely in a large number as shown in the plan view of FIG. 12, thus making it possible to increase the blowing speed of heated-air. Further, the heated-air blowing holes 32a are located so as to be in agreement with a clearance of the planar heater 1 and can be provided freely according to the shape of the planar heater 1, with no particular restriction on the arrangement thereof. Still further, the heated-air blowing holes are provided obliquely, thereby generating a swirling flow without using a mechanism such as a fan to make temperatures uniform more simply. In addition, a way of providing the blowing holes can be set in various directions as shown in the cross sectional views of FIGS. 13(a), (b) and (c). There is no particular restriction on the directions, in addition to those shown in the figure.

Although there is no particular restriction on the number of gas supplying pipes 15, two or more gas supplying pipes may be provided, thereby making it possible to eliminate an unevenness in gas flow and also attain a uniform temperature. The flow rate of gas can also be referred to control the speed of temperature elevation. Further, gas supplied from the gas supplying pipe 15 may by selected, by which it is possible to make an observation under a specific gas atmosphere and also prevent or control oxidation and combustion by injecting an inert gas or others. Still further, the gas supplying pipe 15 may be constituted with a material excellent in X-ray transmission properties, by which the supply of gas can be controlled, with the X-ray transmission properties kept.

Further, on cooling, a coolant gas is allowed to flow through the gas supplying pipe 15. And, a gas supplying pipe exclusively for cooling is provided on the supporting bodies 31, thus making it possible to control cooling rapidly. Thereby, it becomes possible to control rapid cooling and a state of cooling, by which it is possible to observe cooling effects on various phenomena such as a liftoff phenomenon and also conduct a cycle operation between temperature elevation and cooling.

In addition, an exhaust opening 31a may be provided on the supporting body 31 of the heating apparatus, thus making it possible to control the gas atmosphere and flow rate and also control temperatures easily. Further, it is possible to provide a heating apparatus capable of discharging quickly a poisonous gas generated from a sample on heating and high in safety.

In the present embodiment, the planar heater 1 constituted with a material excellent in X-ray transmission properties is used. The planar heater 1 is made of carbon in particular, thereby providing a heater capable of transmitting X-rays and also easily attaining uniform temperature elevation by electrification. In addition, when carbon is used as a material, carbon fibers may be formed into a plane shape and used. Further, where carbon is in particular a carbon-fiber reinforced carbon composite material, electricity will flow easily to generate a heating value according to electric power due to the small electric resistance and easy electrification. This heating is uniform and a carbon-fiber reinforced carbon composite material plate itself is also high in heat conductivity, thus making it possible to elevate the temperature of the planar heater 1 rapidly and uniformly.

Further, an oxidation preventing film may be provided on the surface of carbon, thus making it possible to prevent the oxidation and deterioration of carbon and also improve the durability. Materials of the oxidation preventing film include oxidation preventing films made of titanium diboride and silicon carbide, with no restriction thereon.

The present embodiment is characterized in that a material of the shielded heat isolation part 14 and that of the heated-air blowing plate 32 are any one of ceramics, heat resistant resin, heat resistant rubber, glass, glass fiber, mica and insulation-treated carbon or a combination thereof. These materials are favorable in X-ray transmission properties and also excellent in durability, heat resistance and insulating properties and, therefore, used favorably. More specifically, a plate and a sheet made of alumina ceramics, polyimide resin, silicone resin, fluorocarbon resin, glass, glass fiber, mica or insulation-treated carbon are favorably used. In addition to these materials, the materials can be selected freely depending on a required temperature and strength, with no particular restriction thereon. Further, carbon can be subjected to insulation treatment by various methods such as coating with an insulating material and doping into an insulating agent, with no particular restriction thereon.

The present embodiment is also characterized in that a material of the gas supplying pipe 15 and that of a jig for fixing the shielded heat isolation part 14, the gas supplying pipe 15 or the heated-air blowing plate 32 are any one of ceramics, heat-resistant resin, heat-resistant rubber or a combination thereof. These materials are favorable in X-ray transmission properties and also excellent in durability, heat resistance and insulating properties and, therefore, can be used favorably. More specifically, in addition to these materials, alumina ceramics, polyimide resin, silicone resin and fluorocarbon resin are favorably used, with no particular restriction thereon. The materials can be selected freely depending on a required temperature and strength.

Figure 15:
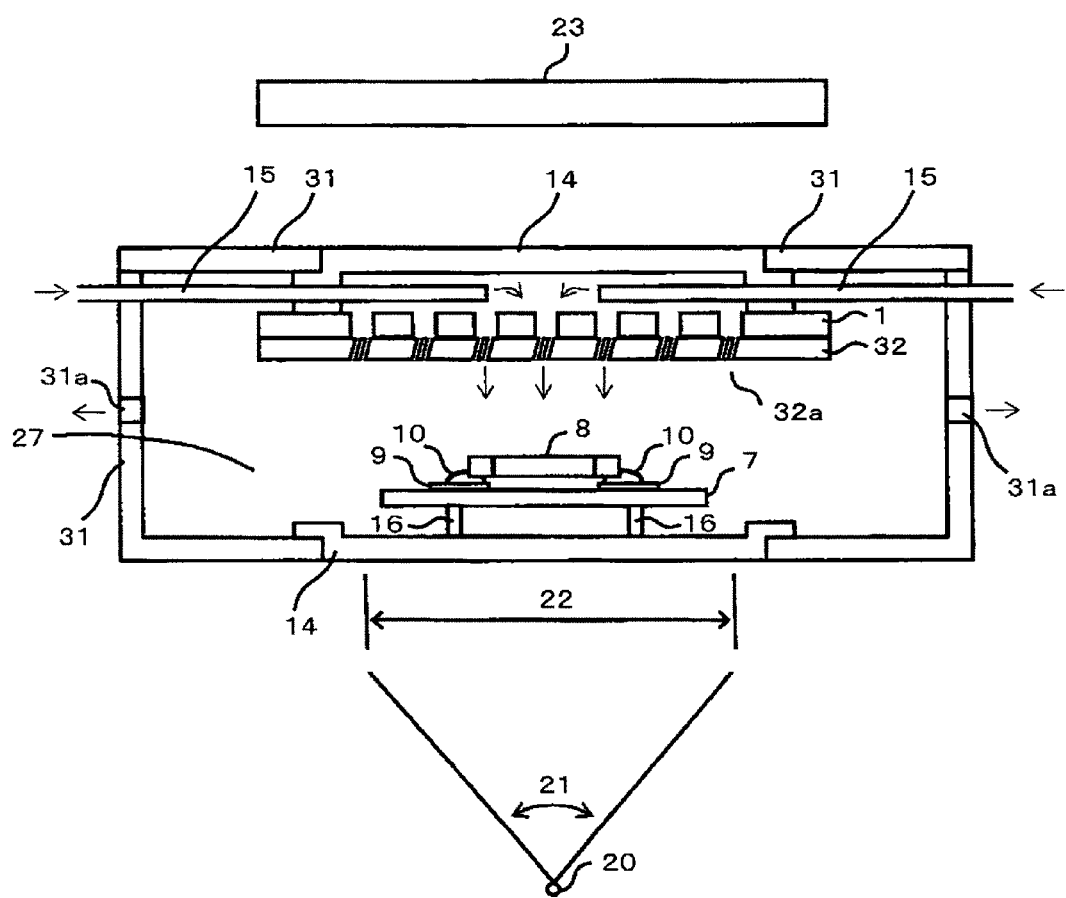
FIG. 15 is also a cross sectional view which shows an entire constitution of Embodiment 5.

The present embodiment is characterized in that it is constituted on rigid supporting bodies 31 which oppose each other, the shielded heat isolation part 14, the planar heater 1 and the heated-air blowing plate 32 are arranged at one of the window part 22 and, of the shielded heat isolation part 14, the planar heater 1 and the heated-air blowing plate 32, at least the shielded heat isolation part 14 is arranged at the other of the window part 22. Thereby, a sample can be heated by selecting a heating method depending on types of the sample, for example, convection heating from both surfaces of the sample as shown in the cross sectional view of FIG. 9, convection heating from one surface (the upper surface in the figure) and thermal conduction heating from the other surface (the lower surface in the figure) as described in Embodiment 3 shown in the cross sectional view of FIG. 14, and convection heating from one surface (the upper surface in the figure) and no heating from the other surface (the lower surface in the figure)

as described in Embodiment 4 shown in the cross sectional view of FIG. 15. Thus, it is possible to provide heating according to a state of the sample.

Figure 16:
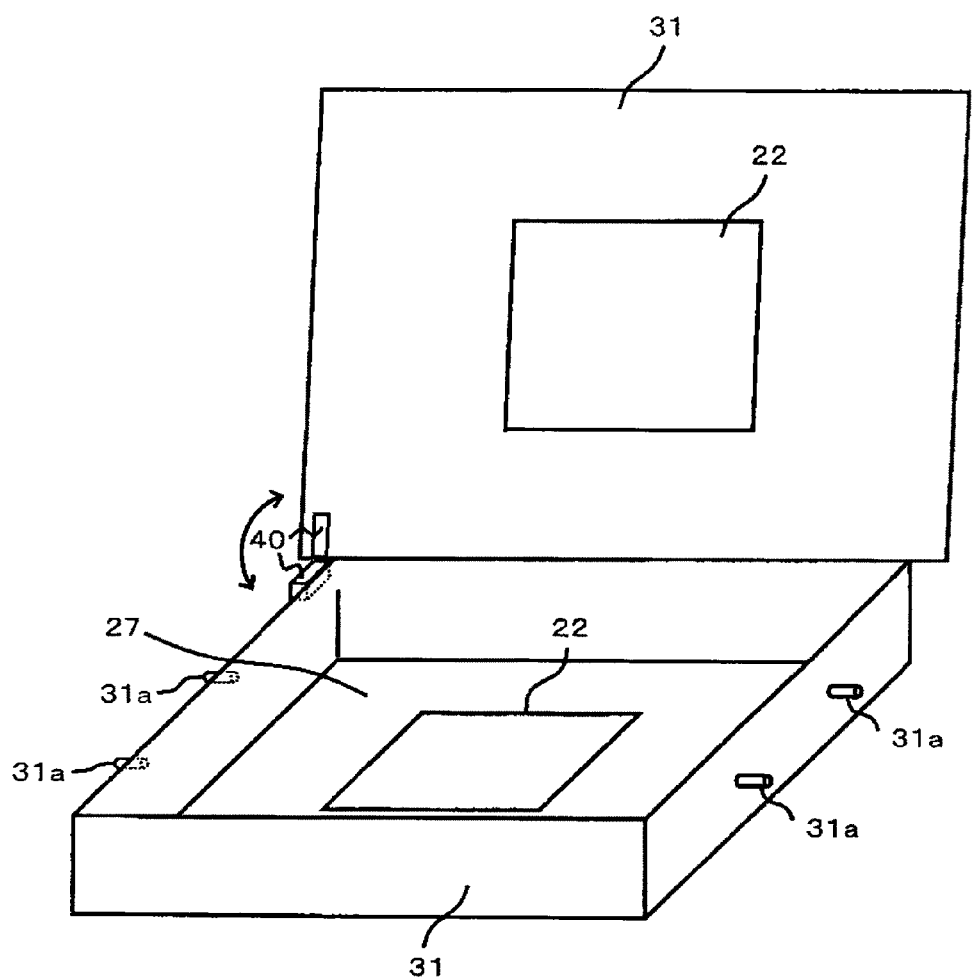
FIG. 16 is also a perspective view which shows one example of a mechanism which allows supporting bodies to oppose each other.

As for a mechanism for allowing the supporting bodies 31 to oppose each other, the supporting bodies 31 can be joined by using a hinge as shown in the perspective view of FIG. 16 so as to be opened and closed. Alternatively, the supporting bodies 31 are allowed to be fitted into or to slide, with no particular restriction on the mechanism.

Further, a limit switch 40 may be installed between the supporting bodies 31, thus making it possible to conduct heating only when the supporting bodies 31 are closed. Therefore, it is possible to prevent an accident. In this instance, since the side of a lid is slightly widened laterally from the side of the main body to install the limit switch 40 outside, the limit switch 40 is less likely to be influenced by high temperatures inside and also the lid can be closed securely.

Still further, as shown in FIG. 1, a pressure sensor 42 may be disposed on the gas supplying pipe 15, thus making it possible to conduct heating only when gas is supplied. Thus, it is possible to prevent an accident such as overheating of the heating apparatus.

In addition, the limit switch 40 and the pressure sensor 42 are required to be provided outside the range of the window part 22.

In the heating apparatus of the present invention, among constituting components, the planar heater 1, the shielded heat isolation part 14 and the heated-air blowing plate 32 are repeatedly subjected to heat cycle and therefore expected to be deteriorated earlier than other components. In particular, where carbon is used as a material constituting the planar heater 1, there is a concern that the planar heater 1 may be deteriorated due to oxidation at a high temperature. Thus, the planar heater 1, the shielded heat isolation part 14, and the heated-air blowing plate 32 provided when necessary may be made available as modules, thereby only worn parts can be exchanged to improve the maintenance and cost performance.

The heating apparatus of the present embodiment is. characterized as being a reflow furnace. Thereby, it is possible to provide a reflow furnace capable of examining a board with an X-ray and easily controlling temperatures.

[Embodiment 1]

Planar heaters made of a carbon-fiber reinforced carbon composite material plate were disposed above and below and formed into the shape shown in FIG. 1. Then, they were used to fabricate a heating apparatus.

[Embodiment 2]

Planar heaters made of a carbon-fiber reinforced carbon composite material plate were disposed above and below and formed into the shape shown in FIG. 9. Then, they were used to fabricate a heating apparatus.

[Embodiment 3]

Planar heaters made of a carbon-fiber reinforced carbon composite material plate and ceramics plates were used to fabricate the heating apparatus shown in FIG. 10 and FIG. 16.

[Embodiment 4]

Figure 14:
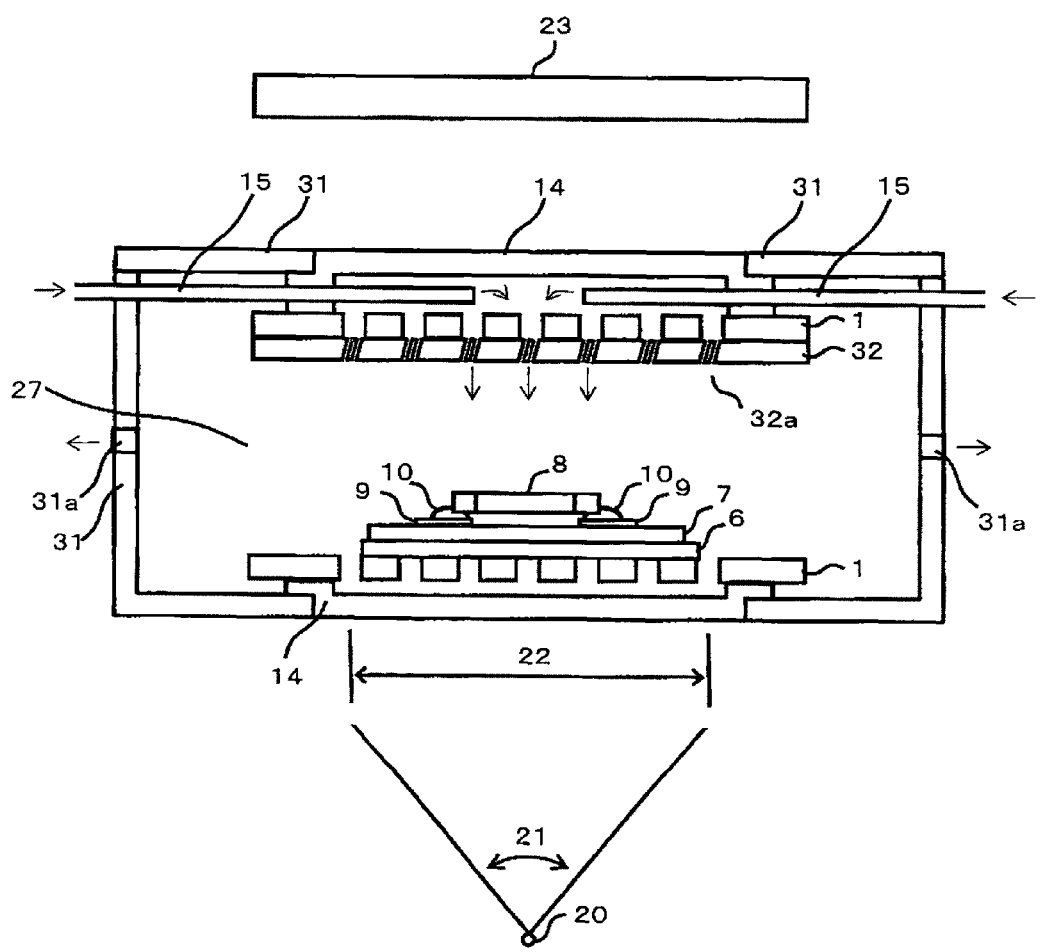
FIG. 14 is a cross sectional view which shows an entire constitution of Embodiment 4 of the heating apparatus for X-ray inspection according to the present invention.

Planar heaters made of a carbon-fiber reinforced carbon composite material plate and ceramics plates were used to fabricate the heating apparatus shown in FIG. 14 and FIG. 16.

[Embodiment 5]

A planar heater made of a carbon-fiber reinforced carbon composite material plate and a ceramics plate were used to fabricate the heating apparatus shown in FIG. 15 and FIG. 16.

[Embodiment 6]

Heaters made of carbon fiber and processed into a plane shape and ceramics plates were used to fabricate the heating apparatus shown in FIG. 10 and FIG. 16.

(Comparative Example 1)

A ceramics heater was used to fabricate a heating apparatus.

(Comparative Example 2)

A sheathed heater having a nichrome wire as a heating source and a blower fan were used to fabricate a heating apparatus.

Any one of the heating apparatuses shown in Embodiments 1 to 6 underwent rapid and uniform temperature elevation according to a predetermined profile. Further, an X-ray observation was able to be made in real time for a motion image in which solder in a melted state vibrated under a ceramics condenser component and jumped out immediately before solidification. The heating apparatus of Comparative example 1 was slow in temperature elevation and unable to effect temperature elevation according to a predetermined profile. The heating apparatus of Comparative example 2 was also slow in temperature elevation, unable to effect temperature elevation according to a predetermined profile and also unable to heat a sample to a required temperature.

INDUSTRIAL APPLICABILITY

The heating apparatus for X-ray inspection is useful in analyzing a cause of defective generation at a solder joint part in particular and able to heat an object to be examined such as a sample to a target temperature or heat it according to a predetermined profile, thereby observing and recording the change in the state in real time.

DESCRIPTION of REFERENCE NUMBERS

1: Planar heater
1a: Metal plate heater
1b: Slit
1c, 1e: Insulating plate
1d, 1f: Gas holes
6: Insulating plate
7: Print circuit board
8: Electronic component
9: Copper land
10: Solder paste
14: Shielded heat isolation part
15: Gas supplying pipe
20: X-ray generating part
21: X-ray irradiation range
22: Window part
23: X-ray receiving apparatus
27: Sample chamber
31: Supporting body
31a: Exhaust opening
32: Heated-air blowing plate
32a: Heated-air blowing hole
40: Limit switch
42: Pressure sensor

The invention claimed is:
1. A heating apparatus for X-ray inspection which heats at least one surface of a sample by convection to perform an X-ray inspection, comprising,
a first planar heater provided at a first window part for making an X-ray observation of the sample,
an X-ray source on one side of the planar heater, and a gas supplying pipe mounted adjacent the planar heater the planar heater comprising a thin metal plate of stainless steel, or an alloy selected from the group consisting of Ni—Cr—Fe, Fe—Cr—Al, Cu—Mn, Cu—Ni, which can transmit X-rays as a whole having a shape of a zigzag type or having holes and electric insulating plate combined with the thin metal plate, a combination of the electric insulating plate and the thin metal plate (1a) has heated-air blowing holes at least a part thereof communicated with each other, the heated-air blowing hole is formed at the electric insulating plate only on the side of a sample and is formed obliquely with retard to surface of the electric insulating plate so as to generate a swirling flow, the heating apparatus is a heating apparatus for X-ray inspection with the thin metal plate (1a) having a thickness equal to or less than 40 μm.

2. The heating apparatus for X-ray inspection according to claim 1, wherein
a second planar heater is disposed on the side of the sample opposite the first planar heater.

3. The heating apparatus for X-ray inspection according to claim 1, wherein
a first shielded heat isolation part formed of an X-ray transmitting material having a gas supplying port is disposed on the first planar heater so as to be overlapped.

4. The heating apparatus for X-ray inspection according to claim 1, wherein
a heated-air blowing plate formed of an X-ray transmitting material having a heated-air blowing hole provided obliquely for smooth convection is disposed on the first planar heater so as to be overlapped.

5. The heating apparatus for X-ray inspection according to claim 3, wherein
the heating apparatus is disposed on first and second rigid supporting bodies having respectively first and second window parts which oppose each other, the first shielded isolation part and the first planar heater are arranged on the first window part, and, of a second shielded heat isolation part and a second planar heater, at least the second shielded heat isolation part is arranged on the second window part.

6. The heating apparatus for X-ray inspection according to claim 5, wherein
the heating apparatus is provided with a gas supplying pipe exclusively for cooling on the supporting bodies.

7. The heating apparatus for X-ray inspection according to claim 5, wherein
the heating apparatus is provided with an exhaust opening on the supporting bodies.

8. The heating apparatus for X-ray inspection according to claim 5, wherein
a pressure sensor for detecting a pressure of gas is disposed on the gas supplying pipe, which is connected to a gas supplying port of the shielded heat isolation part.

9. The heating apparatus for X-ray inspection according to claim 2, wherein
at least the shielded heat isolation part and the planar heater are made available as modules.

10. The heating apparatus for X-ray inspection according to claim 1, wherein
the heating apparatus is a reflow furnace.

* * * * *